US006183756B1

(12) United States Patent
Istrate et al.

(10) Patent No.: US 6,183,756 B1
(45) Date of Patent: Feb. 6, 2001

(54) METHODS FOR PREVENTION AND/OR TREATMENT OF THROMBOCYTOPENIA

(75) Inventors: Nicolae Istrate, Lexington; Gita Muni, North Reading; Edgard Brauner, Brighton; Fazal Raheman, Burlington, all of MA (US)

(73) Assignee: Dynagen, Inc., Cambridge, MA (US)

( * ) Notice: Under 35 U.S.C. 154(b), the term of this patent shall be extended for 0 days.

(21) Appl. No.: 08/846,461

(22) Filed: May 1, 1997

(51) Int. Cl.$^7$ .......................... A61K 39/10; A61K 39/00; A61K 39/38; A61K 39/02

(52) U.S. Cl. .................................. 424/260.1; 260/184.1; 260/234.1

(58) Field of Search .............................. 424/184.1, 234.1, 424/260.1

(56) References Cited

U.S. PATENT DOCUMENTS

| 4,182,751 | 1/1980 | Ayme | 424/92 |
| 4,971,801 | * 11/1990 | Urban | 424/450 |

FOREIGN PATENT DOCUMENTS

| PCT/US97/07340 | 5/1997 | (WO) . |
| PCT/US98/0887 | 7/1998 | (WO) . |

OTHER PUBLICATIONS

Olinescu et al. Rev. Ig Bacteriol Virusol Parazitol Epidemiol Pneumoptiziol Ser Bacteriol 34(4):325–336, 1989 (English Translation.*
Olinescu et al. Neoplasma 38(1):119–128, 1991.*
Bukowski RM (Seminars in Oncology 21/4 Suppl. 7 (96–99), 1994.*
Bukowski RM. Seminars in Oncology 21/4 Suppl. 7(96–99), 1994.*
Negut et al. Arch. Roum. Pathol. Exp. Microbiol. (Romania) 44(4):323–355, 1985.*
PR Newswire P 0331 SE 002 (Mar. 31, 1995).*
Likhite, V., "Experimental Cancer Immunotherapy: Comparison of Tumor Rejection . . . Carynobacterium parvum", *Exp. Cancer Immunother.*, (1976), 985–989.
Anthoy, V., et al., "Bacillus Calmette—Guerin–stimulated Neutrophils Release Chemotaxins for Monocytes in Rabbit Pleural Spaces and in Vitro", *J. Clin. Invest.*, (1985), 76:1514–1521.
Jackson, A., et al., "Inductions of ICAM 1 expression on bladder tumours by BCG immunotherapy", *J. Clin. Invest.*, (1994), 76:1514–1521.
Danforth, J., et al., "Microphage Inflammatory protein–1–alpha expression . . . lipoteichoic acid", *Clin. Immunopath.*, (1995), 74:1, Abstract.
Usami, H., et al., "Antitumour effects of streptococcal lipoteichoic acids on Meth A fribrosarcoma", *Br. J. Cancer*, (1988), 57:70–73.

Ohshima, Y., et al., "Activation of Mononuclear Immune Cells in Response to Staphylococcal Lipoteichoic Acid", *Zbl. Bakt.*, (1991), 275:374–381.

Keller, R., et al., "Macrophage Response to Bacteria: Induction of Marked Secretory and Cellular Activities by Lipoteichoic Acids", *Infect. & Immun.*, (1992), 60:9:3664–3672.

Kusunoki, T., et al., "Molecules from *Staphylococcus aureus* that Bind CD14 and Stimulate Innate Immune Responses", *J. Exp. Med.*, (1995), 182:1673–1682.

Olinescu, A., et al., "Normal Immune Functions Consequent to Cantastim Therapy in a Case of Chronic Lymphatic Leukemia T CLLT", *Rev IG Bacteriol Virusol Parazitol Epidemiol Pneumoftiziol Ser Bacteriol Virusol Parazitol Epidemiol*, (1988) 33:3:281–288.

Marx, A., et al., "Immuno–modulator prepn. from pseudomonas aeruginosa suspension . . . " *Database DPI*, (1986), Abstract.

Olinescu, A., et al., "The effect of non–specific immunostimulation with "Cantastim" on the cell mediated . . . ", *Biological Abstracts*, (1991), 91:1:491.

Ex Parte Forman et al., Appeal No. 602–90, 1986, 230 U.S.P.O . . . pp. 546–549.

Piatak, M., Jr. et al., "High Levels of HIV–1 in Plasma During All Stages of Infection Determined by Competitive PCR", *Science*, 1993, vol. 259, pp. 1749–1754.

Katzenstein, D., M.D. et al., "The Relation of Virologic and Immunologic Markers to Clinical Outcomes Outcomes After Nucleoside Therapy in HIV–Infected Adults with 200 to 500 CD4 Cells per Cubic Millimeter", *The New England Journal of Medicine*, 1996, vol. 335, No. 15, pp. 1091–1098.

Saravolatz, L., M.D. et al. ,"Zidovudine Alone or in Combination with Didanosine or Zalcitabine in HIV–Infected Patients with the Acquired Immunodeficiency Syndrome or Fewer Than 200 CD4 Cells per Cubic Millimeter", *The New England Journal of Medicine*, 1996, vol. 335, No. 15, pp. 1099–1106.

(List continued on next page.)

*Primary Examiner*—Jeffrey Stucker
*Assistant Examiner*—Brett Nelson
(74) *Attorney, Agent, or Firm*—Wolf, Greenfield & Sacks, P.C.

(57) ABSTRACT

The present invention is directed to a method of treating subjects exhibiting thrombocytopenia or at risk of developing thrombocytopenia. The method includes the step of administering to the subject exhibiting thrombocytopenia or at risk of developing thrombocytopenia, an effective amount of a Pseudomonas solvent extract or active fraction thereof. The Pseudomonas solvent extract is administered in an amount effective to increase platelet levels in the subject.

21 Claims, 3 Drawing Sheets

OTHER PUBLICATIONS

Hammer, S., M.D. et al., "A Trial Comparing Nucleoside Monotherapy with Combination Therapy in HIV–Infected Adults with CD4 Cell Counts from 200 to 500 per Cubic Millimeter". *The New England Journal of Medicine*, 1996, vol. 335, No. 15, pp. 1081–1090.

Gupta, S., (edited by), "Immunology of HIV Infection", *Plenum Press*, 1996, 475–491.

Burns, et al., "Treatment of Septic Thrombocytopenia . . . ", *J Clin Immunology*, (1991) 11:6:363–368.

Salageanu, et al., "Experimental Studies on Bacterial . . . ", *Rom. Arch. Microbiol. Imm.*, 1997, 56:1–2:17–26.

Eugenia Negut et al., "Immunomodulation Activity of a *Pseudomonas Aeruginosa* Extract—Cantastim", *Arch. Roum. Path. Exp. Microbiol.*, T., 1985, vol. 44, No. 4, pp. 323–335.

A. Olinescu et al., "In vivo and in vitro effect of Cantastim, an immunomodulatory agent extracted a highly pathogenic *Pseudomonas aeruginosa* strain", *Neoplasma*, 1991, vol. 38, No. 1, pp. 119–128.

* cited by examiner

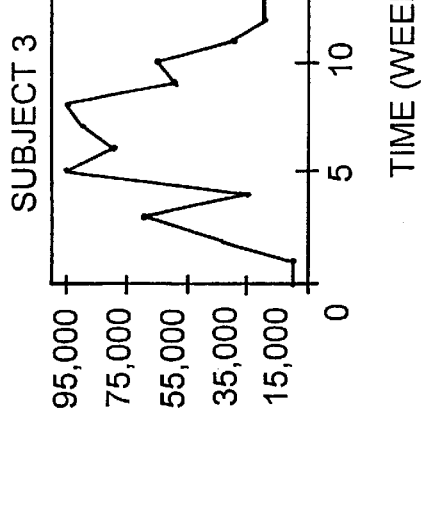
Fig. 2A
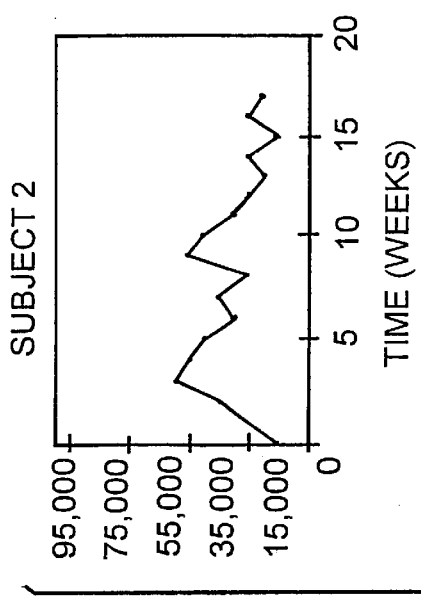
Fig. 2B
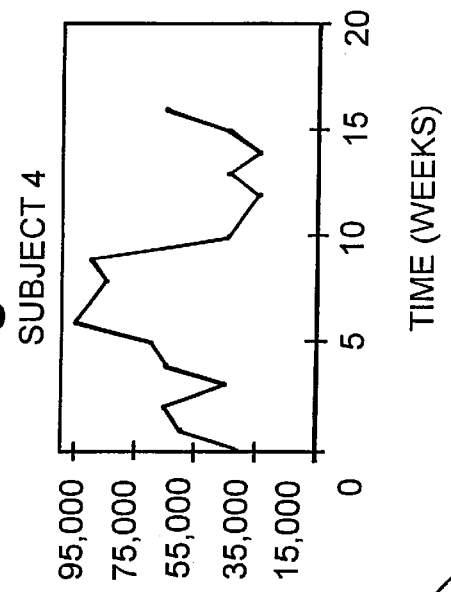
Fig. 2C
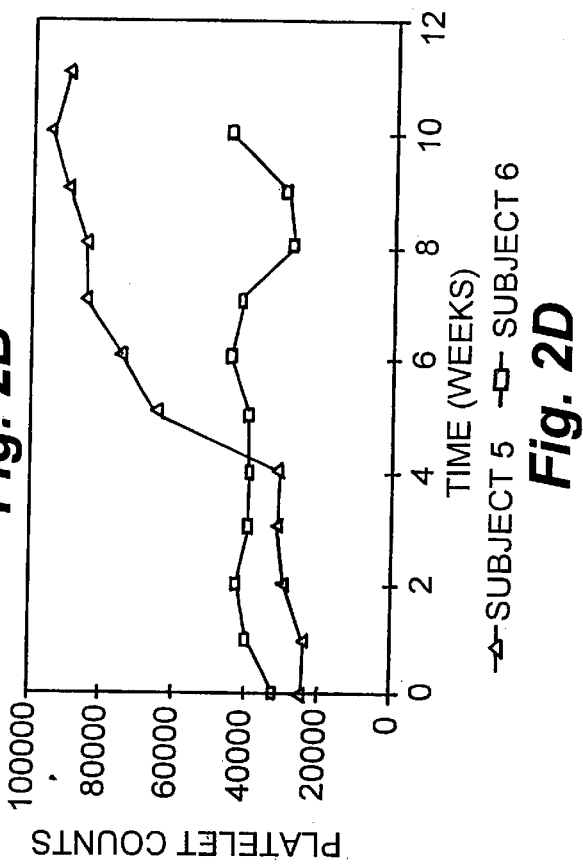
Fig. 2D
Fig. 2

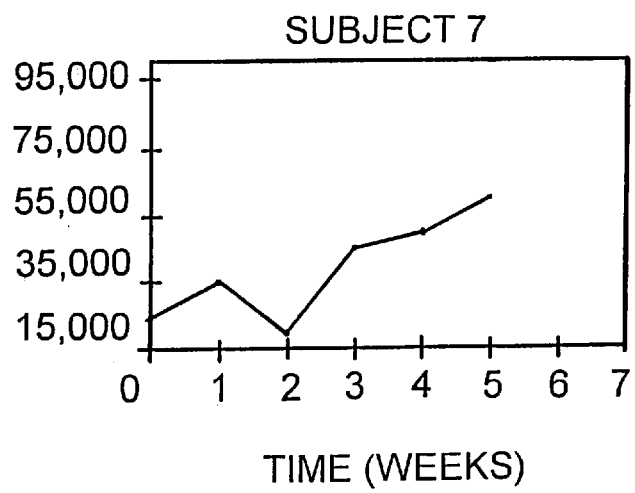
*Fig. 3A*
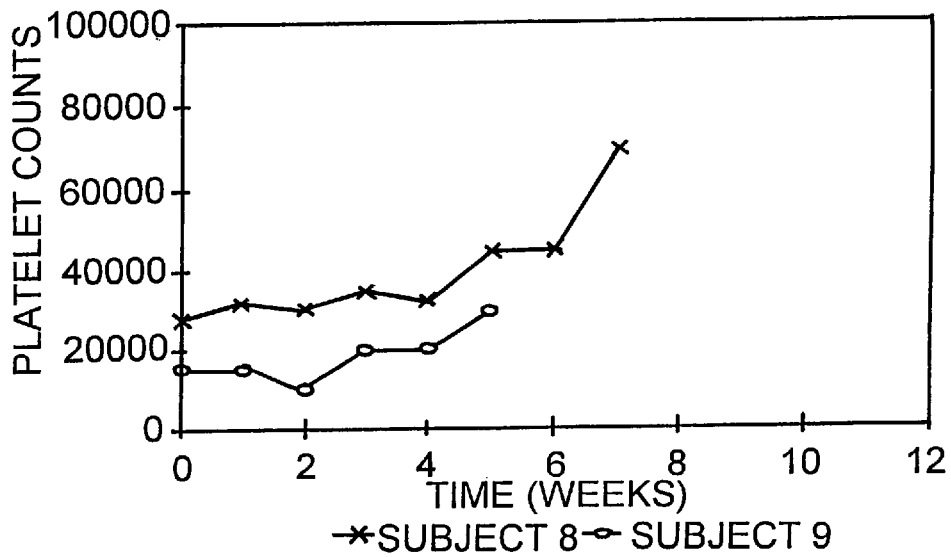
*Fig. 3B*
*Fig. 3*

METHODS FOR PREVENTION AND/OR TREATMENT OF THROMBOCYTOPENIA

FIELD OF INVENTION

This invention pertains to the field of immunopharmacology and, in particular, the use of a solvent extract or active fraction thereof derived from Pseudomonas to increase platelet count in individuals affected with thrombocytopenia, a platelet depletion disorder, or at risk of developing thrombocytopenia.

BACKGROUND

Erythrocytes, leukocytes and platelets are the essential cells of the human hematopoietic system. The primary function of erythrocytes, also known as red blood cells, is to transport hemoglobin, which in turn carries oxygen from the lungs to tissues. Oxygenated hemoglobin gives the erythrocytes a red color. Leukocytes, also referred to as myeloid cells, are a heterogenous group of cells that mediate immune responses and which include granulocytes, monocytes, and lymphocytes. These cells are found predominately in the blood, bone marrow, lymphoid organs and epithelium. Leukocytes are referred to as white blood cells because of a lack of natural pigment which gives the cells a whitish or transparent appearance.

Platelets are small (2–4 μm) anucleate disk-like cells which play an important role in blood coagulation. Platelets are derived by cytoplasmic fragmentation of the precursor stem cells, megakaryocytes, found in bone marrow. After formation, platelets leave the bone marrow and travel through the spleen and into the blood, with approximately one third of the platelets becoming sequestered in the spleen. The platelets which are transported to the blood, circulate for approximately seven to ten days.

Platelets which are normally present in human blood at a concentration of 150,000–400,000 per microliter play a crucial role in hemostasis, or the regulation of bleeding. When the level of platelets falls below normal in a subject, the risk of hemorrhage increases in the subject. The condition associated with low levels of platelets is referred to as thrombocytopenia.

Ordinarily when the level of circulating platelets decreases a feedback mechanism is initiated which results in increased production in the number, size, and ploidy of megakaryocytes. This mechanism, in turn, causes the production and release into the circulation of additional platelets. Although the feed back regulation of platelet levels is ordinarily sufficient to maintain a normal level of platelets in the circulation, several physiological conditions are capable of causing a significant imbalance in the level of platelets. Such conditions result in either thrombocytopenia or thrombocytosis (a condition caused by an increased level of platelets in the blood).

At least three physiological conditions are known to result in thrombocytopenia: a decreased production of platelets in the bone marrow; an increased splenic sequestration of platelets; or an accelerated destruction of platelets. In conventional therapies in order to successfully treat thrombocytopenia, one must first identify which mechanism is causing the decrease in platelet levels and then treat the subject by administering a drug or instituting a procedure which will eliminate the underlying cause of the platelet loss.

A loss of platelets due to decreased production of bone marrow, may be established by the examination of a bone marrow aspirate or biopsy which demonstrates a reduced number of megakaryocytes. A decreased production of bone marrow may result from myelosuppression as a consequence of gamma irradiation, therapeutic exposure to radiation, or cytotoxic drug treatment. Chemicals containing benzene or anthracene and even some commonly used drugs such as chloramphenicol, thiouracil, and barbiturate hypnotics can cause myelosuppression, resulting in thrombocytopenia. Additionally, rare bone marrow disorders such as congenital amegakaryocytic hypoplasia and thrombocytopenia with absent radii (TAR syndrome) can selectively decrease megakaryocyte production, resulting in thrombocytopenia.

Splenic sequestration of platelets can cause an increase in spleen size. Splenic sequestration can often be determined by bedside palpation to estimate splenic size. An increase in spleen size, or splenomegaly, is typically caused by portal hypertension secondary to liver disease, splenic infiltration with tumor cells in myeloproliferative or lymphoproliferative disorders, or macrophage storage disorders such as Gauchers disease. Splenectomy is often used to increase platelet counts in cases of excessive splenic sequestration.

Thrombocytopenia resulting from accelerated destruction of platelets is generally the cause of decreased levels of platelets in the blood when impaired production of bone marrow and splenic sequestration have been ruled out. The accelerated destruction of platelets is caused by either an immunologic disorder or a non-immunologic disorder. Immunologic thrombocytopenia can be caused, for example, by autoimmune disorders such as idiopathic thrombocytopenic purpura (ITP), viral or bacterial infections, and drugs. Non-immunologic thrombocytopenia is caused by vasculitis, hemolytic uremic syndrome, thrombotic thrombocytopenic purpura (ITP), disseminated intravascular coagulation (DIC) and prosthetic cardiac valves. Chronic ITP is often treated with high doses of steroids, intravenous gamma globulins, splenectomy, and even immunosuppressive drugs. Each of these therapeutic modalities provides only temporary relief and is associated with serious side effects. Additionally, approximately 20 percent of the chronic ITP patients do not respond to any of the known treatments.

Factors which induce proliferation and differentiation of megakaryocytes have been proposed as therapeutic treatments for increasing platelet counts, regardless of the mechanism causing thrombocytopenia. Thus far three such factors have been identified, but have not yet been well characterized. A recent report has suggested that the three factors, C-MpL ligand, thrombopoietin, and megakaryocytes colony stimulating factor (MK-CSF) are the same molecule (Wendling F. et al., C-MpL ligand is a humoral regulator of megakaryocytopoesis, Nature, 369; p. 571–574 (1994)). Interleukin 11 has been shown to induce megakaryocytopoesis in an animal model. It is unclear whether these compounds will be effective clinical treatments for thrombocytopenia.

There presently exists a need for therapeutic methods for increasing platelet levels or preventing significant decreases in platelet levels. Ideally, the therapy should eliminate thrombocytopenia in individuals exhibiting thrombocytopenia or prevent thrombocytopenia in individuals at risk of developing thrombocytopenia. Such therapy preferably should be easy and safe to administer and require few diagnostic tests to follow the course of treatment. The patient preferably should be allowed to be treated on an ambulatory basis, thereby reducing the hospital visits while still allowing an improved quality of life. Such therapy preferably should be effective for all types of thrombocytopenias regardless of the underlying physiological condition causing platelet depletion.

SUMMARY OF THE INVENTION

The present invention is directed to methods and products for treating subjects having thrombocytopenia or at risk of developing thrombocytopenia. This includes treatment of mild thrombocytopenia wherein a subject's platelet counts are between 50,000 and 100,000 platelets per microliter, moderate thrombocytopenia wherein the subject has between 20,000 and 50,000 platelet counts per microliter and severe thrombocytopenia wherein the subject has a platelet count of below 20,000 platelets per microliter.

According to one aspect of the invention, a method for treating a subject having thrombocytopenia is provided. The method involves administering to a subject in need of such treatment a Pseudomonas solvent extract or an active fraction thereof that increases, when administered subcutaneously, in vivo circulating platelet counts, in an amount effective to increase platelet counts in the subject. In one embodiment, the Pseudomonas solvent extract or active fraction thereof is administered in an amount effective to increase platelet counts by at least 10,000 platelets per microliter, and more preferably, by at least 20,000 platelets per microliter. In another embodiment, the Pseudomonas solvent extract or active fraction thereof is administered to a subject having less than 50,000 platelets per microliter and in an amount effective to elevate that count to greater than 50,000 platelets per microliter. In still another embodiment, the amount administered is effective to increase the platelet count in a subject by 100%.

In preferred embodiments, the Pseudomonas solvent extract is an extract of *Pseudomonas aeruginosa*. A preferred *Pseudomonas aeruginosa* strain is strain 4922, deposited at the Cantcuzino Institute-Bucharest, Romania. A particularly preferred Pseudomonas solvent extract derived from *Pseudomonas aeruginosa* is sold by Cantcuzino Institute under the trademark CANTASTIM™, other preferred extracts are those having the characteristics of CANTASTIM™ and active fractions thereof. Materials such as CANTASTIM™ are obtainable by incubating acetone with *Pseudomonas aeruginosa* to produce a first precipitate, and then mixing that precipitate with ethanol and collecting ethanol extract. The ethanol extract is precipitated with acetone to form the preferred Pseudomonas solvent extract useful according to the invention. Active fractions thereof are obtainable as described below.

It is preferred that the Pseudomonas solvent extract or active fraction thereof be administered subcutaneously, and most preferably weekly in an amount between 0.1 and 10 mg per dose, most preferably 0.5 mg per dose.

In one embodiment, an effective amount of a solvent Pseudomonas extract or active fraction thereof is 0.1–10.0 mg/dose. Preferably, the amount is in the range of 0.5–1.0 mg/dose. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered weekly for up to fifty-two weeks; more preferably, for one to thirty-two weeks, and even more preferably, for four to fourteen weeks.

Preferably, after a period of administration of the Pseudomonas solvent extract or active fraction thereof, the therapy is discontinued for four to fifty-two weeks and restarted. Even more preferred, the therapy is restarted after eight to fourteen weeks. In some cases, lifelong treatment may be indicated.

In a preferred embodiment, the Pseudomonas solvent extract or active fraction thereof is administered to a subject having thrombocytopenia or at risk of developing thrombocytopenia resulting from treatment with myelosuppressive drugs, e.g., chemotherapy treatments. A preferred manner of administration of the Pseudomonas solvent extract or active fraction thereof for prevention of thrombocytopenia in subjects on myelosuppressive drugs, for example, in the case of chemotherapy for some cancers, is 0.5–1.0 mg/dose administered subcutaneously, once a week for 24 weeks. Preferably, the first dose of the Pseudomonas solvent extract or active fraction thereof is either administered the same day or within 48 hours before the myelosuppressive drug is administered. Additional doses of the Pseudomonas solvent extract or active fraction thereof may be administered with subsequent chemotherapy cycles, usually occurring at monthly intervals.

A preferred manner of administration of the Pseudomonas solvent extract or active fraction thereof is 0.5–1.0 mg/dose administered subcutaneously, once weekly for four to eight weeks. This regimen is restarted after a break of four to eight weeks. The cycle of administration and breaks are repeated as necessary. The effective amount of Pseudomonas solvent extract or active fraction thereof is administered in a solution suitable for subcutaneous administration. A typical solution for administration contains 0.5–1.0 mg/ml of the Pseudomonas solvent extract or active fraction thereof with suitable preservatives, stabilizers, and buffers.

According to another aspect of the invention, a method is provided for treating a subject at risk of becoming thrombocytopenic. The invention involves administering to a subject in need of such treatment a Pseudomonas solvent extract or an active fraction thereof which increases, when administered subcutaneously, in vivo, circulating platelet counts. The Pseudomonas solvent extract or active fraction thereof is administered in an amount effective to prevent a platelet count decrease in the subject to a level below 50,000 platelets per microliter. In some embodiments, the Pseudomonas solvent extract or active fraction thereof is administered in an amount to prevent platelet count in a subject from decreasing from above 100,000 platelets per microliter to below 100,000 platelets per microliter. In another embodiment, the material of the invention is administered in an amount to prevent a decrease in the subject of platelet counts between 50,000 and 100,000 platelets per microliter to below 50,000 platelets per microliter. In still other embodiments, the materials of the invention are administered in amounts to present platelet count from decreasing by more than 15,000 platelets per microliter. In certain embodiments, the subject is at risk of developing thrombocytopenia as a result of planned therapeutic intervention such as by therapeutic exposure to radiation or cytotoxic drug treatment. In these instances, the treatments of the invention are administered in conjunction with such therapeutic interventions. By "in conjunction with" is meant close enough in time with the treatment to have the desired medical effect.

The preferred materials, dosages and the like for treating subjects at risk of developing thrombocytopenia are as described above for subjects having thrombocytopenia.

In one embodiment, an effective amount of a solvent Pseudomonas extract or active fraction thereof is 0.1–10.0 mg/dose. Preferably, the amount is in the range of 0.5–1.0 mg/dose. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered weekly for up to fifty-two weeks; more preferably, for one to thirty-two weeks, and even more preferably, for four to fourteen weeks.

Preferably, after a period of administration of the Pseudomonas solvent extract or active fraction thereof, the therapy is discontinued for four to fifty-two weeks and restarted. Even more preferred, the therapy is restarted after eight to fourteen weeks. In some cases, lifelong treatment may be indicated.

In a preferred embodiment, the Pseudomonas solvent extract or active fraction thereof is administered to a subject having thrombocytopenia or at risk of developing thrombocytopenia resulting from treatment with myelosuppressive drugs, e.g., chemotherapy treatments. A preferred manner of administration of the Pseudomonas solvent extract or active fraction thereof for prevention of thrombocytopenia in subjects on myelosuppressive drugs, for example, in the case of chemotherapy for some cancers, is 0.5–1.0 mg/dose administered subcutaneously, once a week for 24 weeks. Preferably, the first dose of the Pseudomonas solvent extract or active fraction thereof is either administered the same day or within 48 hours before the myelosuppressive drug is administered. Additional doses of the Pseudomonas solvent extract or active fraction thereof may be administered with subsequent chemotherapy cycles, usually occurring at monthly intervals.

A preferred manner of administration of the Pseudomonas solvent extract or active fraction thereof is 0.5–1.0 mg/dose administered, subcutaneously once weekly for four to eight weeks. This regimen is restarted after a break of four to eight weeks. The cycle of administration and breaks are repeated as necessary. The effective amount of Pseudomonas solvent extract or active fraction thereof is administered in a solution suitable for subcutaneous administration. A typical solution for administration contains 0.5–1.0 mg/ml of the Pseudomonas solvent extract or active fraction thereof with suitable preservatives, stabilizers, and buffers.

According to another embodiment of the invention, the subject exhibiting thrombocytopenia according to any of the methods disclosed above has thrombocytopenia selected from the group consisting of infection-induced thrombocytopenia, treatment-induced thrombocytopenia, and physiologically-induced thrombocytopenia. In another embodiment the subject has infection-induced thrombocytopenia. In yet another embodiment the subject has treatment-induced thrombocytopenia. In another embodiment the subject has physiologically-induced thrombocytopenia. In certain embodiments of the invention, the thrombocytopenia preferably is treatment-induced thrombocytopenia. In other embodiments, the thrombocytopenia preferably is autoimmune idiopathic thrombocytopenic purpura.

In yet another aspect of the invention, a use of a solvent extract of Pseudomonas or active fraction thereof in the manufacture of a medicament for treating a subject exhibiting thrombocytopenia is provided. The solvent extract, or active fraction thereof, stimulates mouse splenocyte proliferation in a manner characteristic of CANTASTIM™. In a preferred embodiment the Pseudomonas solvent extract or active fraction thereof is an ethanol and acetone extract of Pseudomonas. Preferably the bacterium is *Pseudomonas aeruginosa*.

According to another aspect of the invention a method of treating thrombocytopenia, in which CANTASTIM™ is administered to a subject in need of such treatment in an amount effective to increase platelet counts in the subject. In one embodiment the CANTASTIM™ is administered in an amount effective to increase platelet counts in the subject by at least 10,000 platelets per microliter, and more preferably by at least 20,000 platelets per microliter.

According to another aspect of the invention a method of treating thrombocytopenia, is provided in which a Pseudomonas solvent extract or active fraction thereof is administered to a subject in need of such treatment, wherein the Pseudomonas solvent extract is obtainable by incubating acetone with a Pseudomonas culture to produce a first precipitate; mixing the first precipitate with ethanol and collecting the ethanol extract and precipitating an active material from the ethanol extract by acetone precipitation to produce the Pseudomonas solvent extract, and wherein the Pseudomonas solvent extract is administered in an amount effective to increase platelet counts in the subject. In one embodiment the Pseudomonas solvent extract is administered in an amount effective to increase platelet counts in the subject by at least 10,000 platelets per microliter, and more preferably by at least 20,000 platelets per microliter.

In one embodiment the Pseudomonas solvent extract is obtained from *Pseudomonas aeruginosa*. In another embodiment the Pseudomonas solvent extract is CANTASTIM™.

Embodiments of the present invention provide a cost-effective therapy for treatment and/or prevention of thrombocytopenia. As discussed in the background of the invention thrombocytopenia may be due to a variety of physiological conditions. The Pseudomonas solvent extract or active fraction thereof may be administered in conjunction with any treatment conventionally used for the treatment of the physiologic condition causing thrombocytopenia. In the case when thrombocytopenia can be caused by angiosupressive drugs, the Pseudomonas solvent extract or active fraction thereof may be administered in conjunction with such drugs in order to prevent the destruction of platelets by the myelosuppressive drugs. In this manner the Pseudomonas solvent extract or active fraction thereof is capable of preventing a subject at risk from developing thrombocytopenia.

The administration of the Pseudomonas solvent extract or active fraction thereof of the invention to subjects exhibiting thrombocytopenia results in clinical improvements in the subjects associated with higher platelet counts such as higher resistance to opportunistic infections and reduced hemorrhaging episodes, and better responses to chemotherapy treatment. Such individuals require less hospitalization time and exhibit an overall improvement in general clinical condition. These individuals also perceive an improvement in the quality of life.

These and other benefits will be apparent to individuals skilled in the art as described more fully in the accompanying detailed description.

The invention also contemplates the of Pseudomonas solvent extracts and active fractions thereof in the preparation of medicaments for treating thrombocytopenia or individuals having thrombocytopenia or individuals at risk at developing thrombocytopenia. The preferred embodiments of this aspect of the invention are described above.

BRIEF DESCRIPTION OF THE DRAWINGS

FIGS. 2A–2D are graphs representing the platelet counts of several subjects with chronic ITP thrombocytopenia over the course of ten to twenty weeks.

FIGS. 3–3B are graphs representing the preliminary results of studies in which subjects with chronic ITP were administered CANTASTIM™ over the course of five to seven weeks.

DETAILED DESCRIPTION OF THE INVENTION

Figure 1:
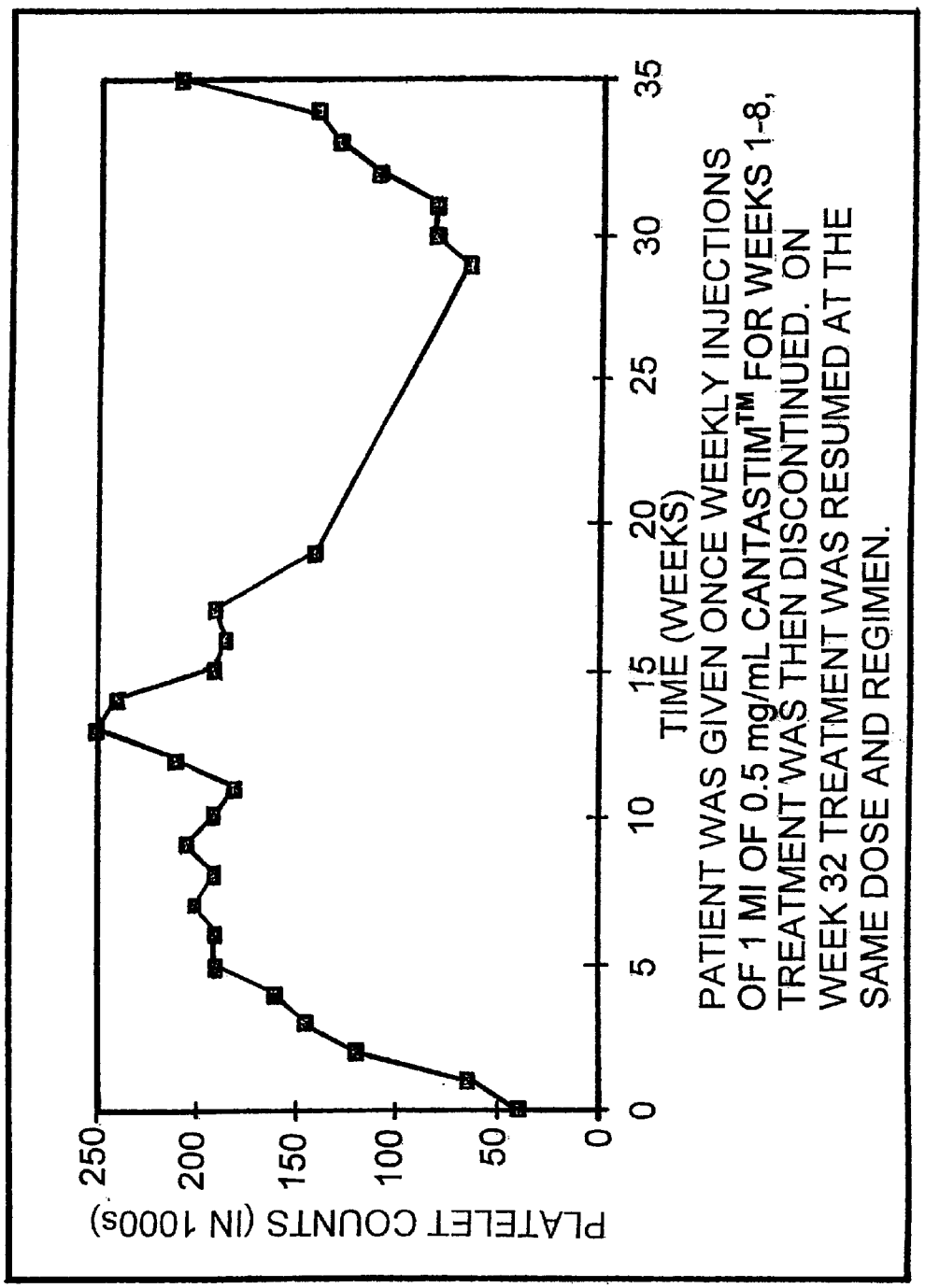
FIG. 1 is a graph representing the platelet counts of a subject with chronic idiopathic thrombocytopenia purpura (ITP) over the course of 35 weeks. The subject was administered CANTASTIM™ for eight weeks and then the therapy was discontinued until week 32, at which point CANTASTIM™ therapy was resumed. A dramatic increase in platelet counts was demonstrated with the initial CANTASTIM™ therapy followed by a decline in platelet counts and an increase in platelet counts upon resumption of CANTASTIM™ therapy.

The present invention is a method of treating thrombocytopenia in a subject exhibiting thrombocytopenia, or at risk of developing thrombocytopenia. As used herein, "thrombocytopenia" is a disorder in which the platelet levels in the affected individual fall below a normal range of platelets for that individual. Mild, moderate, and severe thrombocytopenia are as described above.

Thrombocytopenia includes infection-induced thrombocytopenia, treatment-induced thrombocytopenia, and physiologically-induced thrombocytopenia. Infection-induced thrombocytopenia is a disorder characterized by a low level of platelets in peripheral blood which is caused by an infectious agent such as a bacteria or virus. Treatment-induced thrombocytopenia is a disorder characterized by a low level of platelets in peripheral blood which is caused by therapeutic treatments such as gamma irradiation, therapeutic exposure to radiation, cytotoxic drugs, chemicals containing benzene or anthracene and even some commonly used drugs such as chloramphenicol, thiouracil, and barbiturate hypnotics. Physiologically-induced thrombocytopenia is a disorder characterized by a low level of platelets in peripheral blood which is caused by any mechanism other than infectious agents or therapeutic treatments causing thrombocytopenia. Factors causing physiologically-induced thrombocytopenia include, but are not limited to, rare bone marrow disorders such as congenital amegakaryocytic hypoplasia and thrombocytopenia with absent radii (TAR syndrome), an increase in spleen size, or splenomegaly, caused by portal hypertension secondary to liver disease, or macrophage storage disorders such as Gauchers disease, autoimmune disorders such as idiopathic thrombocytopenic purpura (ITP), vasculitis, hemolytic uremic syndrome, thrombotic thrombocytopenic purpura (TTP) disseminated intravascular coagulation (DIC) and prosthetic cardiac valves.

As used herein, "a subject at risk of developing thrombocytopenia" is a subject who has a high probability of acquiring or developing thrombocytopenia. For example, a patient with a malignant tumor who is prescribed a chemotherapeutic treatment is at risk of developing treatment-induced thrombocytopenia and a subject who has an increased risk of exposure to infectious agents is at risk of developing infection-induced thrombocytopenia.

One embodiment of the present invention is a method of treating thrombocytopenia. The method comprises the step of administering to a subject exhibiting thrombocytopenia a solvent extract of Pseudomonas or active fraction thereof, that stimulates when administered subcutaneously in vivo an increase in platelet counts in a thrombocytopenic mammal.

The Pseudomonas solvent extract or active fraction thereof is administered in an amount effective to increase platelet counts in the subject. An amount effective to increase platelet counts in the subject is an amount which causes an increase in the count of circulating platelet levels. The actual levels of platelets achieved will vary depending on many variables such as the initial status of the immune system in the subject, i.e., whether the subject has mild to severe thrombocytopenia (e.g., resulting from an autoimmune disease or splenic sequestration). In general, the platelet levels of a subject who has severe thrombocytopenia will initially be very low. Any increase in the platelet levels of such a subject, even increases to a level which are still below a normal level, can be advantageous to the subject.

The platelet levels of a subject at risk of developing thrombocytopenia, on the other hand, are generally within a normal range. The Pseudomonas solvent extract or active fraction thereof prevents the platelet levels of such a subject from decreasing to a level which would cause thrombocytopenia. Thus, administering the Pseudomonas solvent extract fraction to the subject will inhibit to a medically significant extent, the decrease in platelet count that would otherwise occur in the absence of treatment according to the invention thereby preventing the development of thrombocytopenia. Preferably the effective amount is one which prevents platelet levels from decreasing below a level of 50,000 platelets per microliter.

An effective amount of a Pseudomonas solvent extract or active fraction thereof for increasing platelet levels may be measured by any conventional method known in the art for measuring platelet levels or for measuring parameters which correlate with platelet levels. Platelet count is determined simply by obtaining a blood sample and counting the number of platelets per microliter of blood. Platelet count also can correlate with bleeding time, a measure of platelet levels.

The Pseudomonas solvent extract or active fraction thereof is derived from Pseudomonas.

A preferred Pseudomonas solvent extract or active fraction thereof is derived from strain 4922 of *Pseudomonas aeruginosa*. A preferred Pseudomonas solvent extract or active extract thereof is sold by Cantacuzino Institute, Bucharest, Romania under the trademark CANTASTIM™.

The Pseudomonas solvent extract or active fraction thereof may be prepared by a solvent extraction of Pseudomonas. For example, pelleted Pseudomonas may be incubated with acetone to produce a first precipitate and then the active components of the first precipitate extracted with ethanol. Other hydrophilic solvents may, of course, be used in place of ethanol (e.g., water, lower alkyl, alcohols). As will be understood by one of ordinary skill in the art, multiple ethanol extractions may be performed to further refine the active fraction. The active fraction may be precipitated by acetone to produce the Pseudomonas solvent extract or active fraction thereof of the invention. Indeed, as will be understood by one of ordinary skill in the art, a variety of fractionation and separation techniques (e.g., chromatography, dialysis, filtration, electrophoresis) may be employed in various orders and multiplicities to further refine the Pseudomonas solvent extract or active fraction thereof and to isolate the active ingredient(s).

Briefly, solvent extraction procedures are performed by addition of a solvent or mixture of solvents to differentially dissolve or extract either active or inactive components from the mixture in such a way that the active components are enriched in either the insoluble material (residue) or in the resulting solution (extract). Solvent crystallization or precipitation procedures are carried out by causing either active or inactive components of the mixture to crystallize or precipitate from solution so that they can be separated from the remaining solution by a technique such as filtration or sedimentation. Solvent precipitation can employ a single solvent or a mixture of solvents and relies on changes in temperature and/or addition of other solvents and/or solutes to differentially affect the solubility of the components of the original mixture. Solvent partition procedures utilize mixtures of solvents to form two or more immiscible phases that can be separated from each other physically and which will result in the differential distribution of active and inactive components between phases, based on the varying solubility of the components in the respective solvents.

A wide variety of chromatographic procedures can be used to produce sample fractions containing active components at higher levels of enrichment than existed in the original sample. The types of chromatographic supports (stationary phase, adsorbent, column packing, etc.) that can be utilized in these separations include the following: 1) normal phase chromatography using any of a variety of polar chromatographic supports (adsorbents) along with a wide variety of elution solvents; 2) reverse phase chromatographic methods using any of a variety of hydrophobic chromatographic supports with any of a variety of elution solvents; 3) ion exchange chromatographic methods using any of a variety of either anionic, cationic, or mixed anionic and cationic chromatographic supports, with a wide variety of elution solvents containing any of a wide variety of ionic modifiers; 4) various types of gel permeation or size exclusion chromatography; and 5) partition chromatography utilizing a stationary liquid phase with a liquid mobile phase. Other methods may also be used to differentially separate active from inactive components of a mixture, including, but not limited to, ultrafiltration, dialysis, electrophoresis, reverse osmosis, and selectively permeable membrane separations.

At each step of such fractionation or separation, one may, without undue experimentation, perform the simple tests discussed below to determine which fraction contains the active ingredient.

The following example of a procedure for preparing the Pseudomonas solvent extract of the invention is provided for illustrative purposes only. (Marx, A., Petcovici, M.: "Immunochemical Studies on Purified Common Enterobacterial Antigen (Kunin)", *Zbl. Bakt. Hys.* 1 Hbt Orig., 233 1975 486). A strain of Pseudomonas bacteria, such as *Pseudomonas aeruginosa* strain 4922 (Cantacuzino Institute), is grown in culture in suitable media. The bacteria are pelleted by centrifugation at 3,000×g for 30 minutes or in a continuous flow centrifuge. Acetone is added to the biomass and the slurry is kept at 2–8° C. for 18 hours. The acetone is decanted and the remaining acetone is allowed to evaporate. 2,000 ml of 95% ethanol is added to 200 g moist microbial mass. The bacteria suspended in ethanol are heated to 60° C. with constant mixing for 20–30 minutes then cooled to 20° C. The bacteria are filtered and the filtrate is concentrated by rotary evaporation to a viscous fluid (complete drying is avoided). This viscous fluid is redissolved in 40 mL 85% ethanol. The soluble phase is decanted into a centrifuge tube and precipitated with 3 volumes of acetone. The whole mixture is spun down for 5 minutes at 6,000×g. The supernatant is discarded and the sediment is dissolved in 4 milliliters distilled water and boiled in a water bath for 30 minutes to produce the Pseudomonas solvent extract.

The effectiveness of a Pseudomonas solvent extract or active fraction thereof in increasing platelet levels or preventing a decrease in platelet levels may be evaluated by one or more simple biological tests. Additionally the extract may be tested in mammals. If a thrombocytopenic mammal displays an increase in circulating platelet levels as a result of treatment, then the fraction is "an active fraction" according to the invention and may be used to increase platelet levels in thrombocytopenic subjects or prevent a decrease in platelet levels in a subject at risk of developing thrombocytopenia. Tests for analyzing the extract in humans may also be performed as described in the Examples.

Other assays, including in vitro assays, correlate with the ability of an "active fraction" to stimulate platelet counts in a mammal. These in vitro assays may be used as preliminary screens to identify "active fraction" according to the invention. Among these are the following.

(1) Determination of the ability of the Pseudomonas solvent extract or active fraction thereof of the invention to stimulate splenocyte proliferation. If the Pseudomonas solvent extract or active fraction thereof exhibits the ability to stimulate murine splenocyte proliferation, the extract may be effective for treating thrombocytopenia in humans. For example, the following assay is a suitable in vitro assay for determining whether a Pseudomonas solvent extract or active fraction thereof is effective.

In vitro Splenocyte Proliferation Assay:

Approximately 1 million splenocytes per mL are isolated from a Balb/C mouse. The splenocytes are tested for proliferative responses to a range of concentrations of the Pseudomonas solvent extract or active fraction thereof by standard methods known to those of skill in the art such as those described in Olinescu et. al., *Neoplasma* v. 38, p. 119 (1991). Negative and positive controls can be employed and the proliferative response of the test sample can be compared to the response in the control samples. Suitable negative controls include saline and cell culture medium. Suitable positive controls include a range of concentrations of materials such as phytohemagglutinin, lipopolysaccharide, and concavalin A. Briefly, the splenocytes are incubated with each of the test samples and each of the controls for three days. The cells are then pulsed with $^3$H-thymidine for 4 hours. The cells are harvested and counted in a beta scintillation counter. Solvent extracts useful for treating thrombocytopenia according to the invention and the positive control samples exhibit a proliferative response at least approximately 50% higher than the negative controls, and can stimulate a proliferative response as great as five times higher or more.

(2) Determination of the ability of the Pseudomonas solvent extract or active fraction thereof of the invention to stimulate cytokine production in human peripheral blood mononuclear cells (PBMCs). If the Pseudomonas solvent extract or active fraction thereof exhibits the ability to stimulate cytokine production in PBMCs, the extract may be considered as a compound which is effective for treating thrombocytopenia. For example, the following assay is a suitable in vitro assay for determining whether a Pseudomonas solvent extract or active fraction thereof is effective in increasing platelet levels In vitro Assay measuring Cytokine production in PBMCs:

Human whole blood is collected in heparin and PBMCs are isolated. The viability of PBMCs are determined by trypan blue exclusion. Viable PBMCs are resuspended in culture medium (2 million cells per mL) and delivered to the wells of tissue culture dishes. A range of concentrations of the Pseudomonas solvent extract or active fraction thereof and of negative and positive controls are added to the wells.

Concentrations of the test samples between approximately 0.015 μg/ml and 0.05 μg/ml are preferred and often demonstrate the largest increases in cytokine levels. Suitable negative controls include saline and cell culture medium. Suitable positive controls include a range of concentrations of material such as previously approved lots of CANTASTIM™ (a suitable range of concentrations of CANTASTIM™ is illustrated in Olinescu et. al., *Neoplasma* v. 38, p. 119 (1991)) and phytohemagglutinin. The cells in the tissue culture wells are incubated overnight. The next day the supernatant fluids are harvested and frozen at −70° C. The supernatant fluids are then assayed to determine the presence or absence of various cytokines, such as TNF, IL1 and IL6. A response in such an assay that is similar to that of previously approved lots of CANTASTIM™ indicates that the sample is effective as a Pseudomonas solvent extract or active fraction thereof according to the invention.

(3) Determination of the ability of the Pseudomonas solvent extract or active fraction thereof of the invention to nonspecifically protect mice in an in vivo assay. It has been discovered that the following in vivo non-specific protection assay in mice is useful in determining whether a sample extract is useful for treating thrombocytopenia.

In vivo non-specific protection assay in mice:

Approximately 40 mice are administered each sample extract via intraperitoneal injection. As a negative control approximately 40 mice are injected with saline. After 3 days all mice are challenged with 8 levels (ranging from approximately 600 million bacteria per mouse to 5 million bacteria per mouse) of a pathogenic strain of Pseudomonas aeruginosa, strain PA7 (thus 5 mice from each group will receive the same bacterial dose). The mice are observed for mortality over the next 4 days. The lethal dose that kills 50% of the mice($LD_{50}$) is determined for each group (including the controls). The non-specific protection index of the various sample solvent extracts or controls is calculated by subtracting the $LD_{50}$ in the control group from the $LD_{50}$ in the various treatment groups. A Pseudomonas solvent extract or active fraction thereof is considered to be useful for treating thrombocytopenia if the non-specific protection index is $\geq 1$.

The preparations of the invention are administered in effective amounts. An effective amount of a Pseudomonas solvent extract or active fraction thereof is that amount that will alone, or together with further doses, desirably modulate platelet levels such as by increasing the circulating level of platelets of a subject. It is believed that doses ranging from 1 nanogram/kilogram to 100 milligrams/kilogram, depending upon the mode of administration, will be effective. The preferred range is believed to be between 0.1 and 10.0 mg/dose, particularly if given subcutaneously. More preferably, the amount is in the range of 0.5–1.0 mg/dose. Preferably, the effective amount is administered more than once. Preferably, the effective amount is administered every day to every thirty days and, more preferably, every five to fifteen days. This regimen can be maintained for up to six months to one year, or even the life of a subject. Preferably, the effective amount is administered once weekly for up to fifty-two weeks; more preferably, for up to thirty-two weeks, and even more preferably, for four to fourteen weeks. The absolute amount will depend upon a variety of factors (including whether the administration is in conjunction with other methods of treating thrombocytopenia, the number of doses and individual patient parameters including age, physical condition, size and weight) and can be determined with routine experimentation. It is preferred generally that a maximum dose be used, that is, the highest safe dose according to sound medical judgment.

Preferably, after a period of administration of the Pseudomonas solvent extract or active fraction thereof, the therapy is discontinued for four to 52 weeks and restarted. Even more preferred, the therapy is restarted after eight to fourteen weeks.

A preferred manner of administration of the Pseudomonas solvent extract or active fraction thereof is 0.5–1.0 mg/dose weekly for four to eight weeks and discontinued. Administration is restarted after a period of four to eight weeks. This cycle of administration and breaks is repeated as necessary.

The effective amount, of Pseudomonas solvent extract or active fraction thereof is usually administered in a solution suitable for subcutaneous administration. A typical solution for subcutaneous administration contains 0.5 to 1.0 mg extract/m with suitable preservatives, buffers and salts. The solvent extract, however, may be administered by any method known in the art, such as intramuscular, subcutaneous, or intravenous injection, or by oral, rectal or transdermal delivery forms. A preferred route of administration is by subcutaneous injection.

For purposes of quantifying the amount of Pseudomonas solvent extract or active fraction thereof in a preparation, and for purposes of definiteness in the appended claims, it is necessary to recognize that a Pseudomonas solvent extract or active fraction thereof may be concentrated or dilute and, therefore, a greater quantity of dilute extract will be needed to achieve the same utility as any given quantity of concentrated extract. A preparation containing, comprising or including X % Pseudomonas solvent extract or active fraction thereof by weight, therefore, is defined as a preparation in which the Pseudomonas solvent extract or active fraction thereof if concentrated, would constitute X % by weight. A concentrated Pseudomonas solvent extract or active fraction thereof shall be defined as one losing no more than 25% of its weight upon drying.

Embodiments of the present invention provide clinical benefits to subjects exhibiting thrombocytopenia or at risk of developing thrombocytopenia. These benefits are highlighted in the Examples which follow.

EXAMPLES

Example 1

The effect of CANTASTIM™ on the peripheral blood profile of 22 subjects undergoing cancer chemotherapy in an open label, randomized, controlled trial was studied. The principal inclusion criteria was a recent diagnosis of chemotherapy-sensitive malignancies and a willingness to undergo multiple cycles of a chemotherapy regimen. Ten of the subjects, hereinafter referred to as the test subjects, received the Pseudomonas solvent extract or active fraction thereof, purchased under the trademark CANTASTIM™ (Cantacuzino Institute-Bucharest, Romania). The test subjects were administered subcutaneous injections of the extract once weekly for 12 consecutive weeks. The test subjects were also administered chemotherapy in three cycles of one month each. The first extract injection was administered before the chemotherapy dosing session, either on the same day or 48 hours prior to starting chemotherapy.

Twelve control subjects were matched to the test subjects for similarity of drug regimen, type of cancer and age. The control subjects did not receive any CANTASTIM™ but only received chemotherapy treatments in three cycles of one month each.

Routine laboratory investigations such as vital signs were performed at the start of the study and at several points throughout the course of the study. Clinical evaluation and complete blood counts were performed twice a week during the course of the study.

The results were analyzed to evaluate the extent of reduction of myelosuppression by the CANTASTIM™ of the invention. Although the doses of chemotherapy used in this study were not high enough to cause clinical thrombocytopenia, there was obvious and reproducible reductions in platelet counts of the control subjects as a result of chemotherapy. The platelet reduction ratios were calculated based on the prestudy platelet count and lowest platelet count of the final chemotherapy cycle. The results are shown in Table 1 below. There was a strong trend indicating an increase in platelet counts in the test group when compared to the control group. This approached statistical significance when F-test was used for analyzing the ratios (P=0.048).

TABLE 1

| Subject | Prestudy Platelet Count (per microliter) | Final Platelet Count (per microliter) | Platelet Reduction Ratio |
| --- | --- | --- | --- |
| Control Subjects | 315,000 | 148,000 | 0.478 |
| Test Subjects | 282,000 | 159,000 | 0.594 |

Example 2

The clinical benefits of the Pseudomonas solvent extract or active fraction thereof of the invention were evaluated in a pilot study involving ten patients of chronic idiopathic thrombocytopenic purpura (I.T.P.) The study subjects had sustained low levels of platelets (less than 50,000) for a period of more than three months to several years. The patients were also selected based on previous poor responses to steroid therapy and all patients were willing to participate in the study, were HIV negative and were not pregnant. Additionally each patient was monitored prior to the initiation of the study for CBC, including platelet count, coagulation profile including BT, CT, PT, PTT, thrombin time, factor 13 screening and fibrinogen, bone marrow examination, rheumatoid factor antinuclear antibody, antiplatelet antibody, serum protein electrophorese, and biochemical profile, including LFT, KFT, LDH and electrolytes.

CANTASTIM™ (solvent extract) ampules were purchased from Cantacuzino Institute, Bucharest, Romania.

Each subject was administered 1 ml of 0.5 mg/ml CANTASTIM™ by subcutaneous injection once weekly for eight weeks. The treatment was discontinued thereafter. Each subject was monitored clinically for any bleeding disorders, and CBC and platelet counts were performed twice weekly. In some cases the subjects were symptomatic for bleeding disorders at the start of the study. Each of these subjects were concurrently treated with steroids until the symptoms subsided.

Four of the six subjects completing the study demonstrated dramatic increases in platelet counts which correlated to the administration of CANTASTIM™. Of the ten subjects involved in the study only six subjects completed the study because one subject died from intracranial hemorrhage during the second week of the study and three others began the treatment at a later date and are still undergoing therapy. The result of the study are shown in FIGS. 1–3, discussed further below.

FIG. 1 shows the effect of CANTASTIM™ treatment of subject #1 with chronic idiopathic thrombocytopenia purpura. CANTASTIM™ was administered once weekly for 8 weeks. The therapy was then discontinued until week 32. The platelet counts of subject #1 increased dramatically until approximately 12 weeks, reaching a peak platelet count of 250,000, at which point the platelet counts began to decline. By week 30 the platelet counts had dropped to 60,000. The results in subject #1 demonstrated that the platelet counts increase dramatically in response to CANTASTIM™ treatment and also that platelet counts decreased upon withdrawal of treatment with CANTASTIM™. At week 32 CANTASTIM™ therapy was resumed and platelet counts again dramatically increased in the subject in response to CANTASTIM™. After eight additional injections of CANTASTIM™ the platelet counts of subject #1 increased to 240,000.

FIG. 2 shows the results of CANTASTIM™ treatment in each of the other subjects that completed the study (subjects #2–6). Each of subjects 2–6 were treated with CANTASTIM™ for eight weeks and then the therapy was discontinued. Each of subjects #3, 4, and 5 demonstrated a significant response to CANTASTIM™. The platelet counts of each of these subjects increased dramatically by eight to ten weeks of treatment and then dropped off as the treatment was discontinued. Subjects #2 and 6 did not appear to respond to CANTASTIM™ therapy.

The preliminary results of each of the subjects (subjects #7–9) which began CANTASTIM™ treatment but which have not completed the full cycle of treatment are shown in FIG. 3.

The results clearly demonstrate that CANTASTIM™ is effective in increasing platelet counts in subjects with chronic ITP.

Each of the foregoing patents, patent applications and references is herein incorporated by reference in its entirety. Having described the presently preferred embodiments, in accordance with the present invention, it is believed that other modifications, variations and changes will be suggested to those skilled in the art in view of the teachings set forth herein. It is, therefore, to be understood that all such variations, modifications, and changes are believed to fall within the scope of the present invention as defined by the appended claims.

We claim:

1. A method for treating a subject having thrombocytopenia comprising:
   subcutaneously administering to a subject in need of such treatment a Pseudomonas acetone extract or an active fraction thereof, in an amount effective to increase platelet counts in the subject.

2. The method of claim 1 wherein the Pseudomonas acetone extract or active fraction thereof is administered in an amount effective to increase platelet counts in the subject by at least 10,000 platelets per microliter.

3. The method of claim 1 wherein the Pseudomonas acetone extract or active fraction thereof is administered in an amount effective to increase platelet counts in the subject by at least 20,000 platelets per microliter.

4. The method of claim 1 wherein the Pseudomonas acetone extract or active fraction thereof is administered to a subject having a platelet count below 50,000 platelets per microliter in an amount effective to increase the platelet counts in the subject to above 50,000 platelets per microliter.

5. The method of claim 1 wherein the Pseudomonas acetone extract or active fraction thereof is administered to the subject in an amount effective to increase the platelet counts in the subject by 100%.

6. The method of claim 1 wherein the Pseudomonas acetone extract or active fraction thereof is administered subcutaneously.

7. The method of claim 1 wherein the Pseudomonas acetone extract or active fraction thereof is administered daily.

8. The method of claim 1 wherein the Pseudomonas is *Pseudomonas aeruginosa*.

9. The methods of claim 1 wherein the Pseudomonas acetone extract or active fraction thereof is a *Pseudomonas aeruginosa* extract obtained by incubating acetone with a *Pseudomonas aeruginosa* culture to produce a first precipitate, mixing the first precipitate with ethanol and collecting the ethanol extract, and precipitating the Pseudomonas acetone extract from the ethanol extract by acetone precipitation.

10. The method of claim 1 wherein the thrombocytopenia is a drug-induced thrombocytopenia.

11. The method of claim 1 wherein the thrombocytopenia is an autoimmune idiopathic thrombocytopenic purpura.

12. A method of treating thrombocytopenia, comprising:
administering to a subject in need of such treatment a Pseudomonas acetone extract or active fraction thereof, wherein the Pseudomonas acetone extract is obtainable by incubating acetone with a Pseudomonal culture to produce a first precipitate; mixing the first precipitate with ethanol and collecting the ethanol extract and precipitating an active material from the ethanol extract by acetone precipitation to produce the Pseudomonas acetone extract, and wherein the Pseudomonas acetone extract is administered in an amount effective to increase platelet counts in the subject.

13. The method of claim 12 wherein the Pseudomonas acetone extract is administered in an amount effective to increase platelet counts in the subject by at least 10,000 platelets per microliter.

14. The method of claim 12 wherein the Pseudomonas acetone extract is administered in an amount effective to increase platelet counts in the subject by at least 20,000 platelets per microliter.

15. The method of claim 12 wherein the Pseudomonas acetone extract is obtained from *Pseudomonas aeruginosa*.

16. A method of treating a subject at risk of developing thrombocytopenia comprising:
subcutaneously administering to a subject at risk of developing thrombocytopenia a Pseudomonas acetone extract or an active fraction thereof that increases circulating platelet counts in an amount effective to prevent platelet counts in the subject from decreasing below 50,000 platelets per microliter.

17. The method of claim 16 wherein the subject at risk of developing thrombocytopenia has a disorder treated with myelosuppressive drugs.

18. The method of claim 16 wherein the Pseudomonas acetone extract or active fraction thereof is administered to the subject in an amount effective to prevent the platelet counts in the subject by decreasing by more than 50,000 platelets per microliter.

19. The method of claim 18 wherein the Pseudomonas acetone extract or active fraction thereof is administered subcutaneously.

20. The method of claim 16 wherein the Pseudomonas is *Pseudomonas aeruginosa*.

21. The method of claim 16 wherein the Pseudomonas acetone extract or active fraction thereof is a *Pseudomonas aeruginosa* extract obtained by incubating acetone with a *Pseudomonas aeruginosa* culture to produce a first precipitate, mixing the first precipitate with ethanol and collecting the ethanol extract, and precipitating the Pseudomonas acetone extract from the ethanol extract by acetone precipitation.

* * * * *